US012589015B2

(12) United States Patent
Kasama et al.

(10) Patent No.: US 12,589,015 B2
(45) Date of Patent: Mar. 31, 2026

(54) STENT DELIVERY SYSTEM, ENDOSCOPE SYSTEM, AND STENT INDWELLING METHOD

(71) Applicant: OLYMPUS CORPORATION, Tokyo (JP)

(72) Inventors: Mitsuru Kasama, Sagamihara (JP); Yoichi Sakurada, Higashimurayama (JP)

(73) Assignee: OLYMPUS CORPORATION, Tokyo (JP)

( * ) Notice: Subject to any disclaimer, the term of this patent is extended or adjusted under 35 U.S.C. 154(b) by 889 days.

(21) Appl. No.: 17/888,695

(22) Filed: Aug. 16, 2022

(65) Prior Publication Data

US 2022/0387202 A1     Dec. 8, 2022

Related U.S. Application Data

(63) Continuation of application No. PCT/JP2020/006690, filed on Feb. 20, 2020.

(51) Int. Cl.
A61F 2/966     (2013.01)
A61B 1/00     (2006.01)
(Continued)

(52) U.S. Cl.
CPC .......... A61F 2/966 (2013.01); A61B 1/00119 (2013.01); A61B 1/00154 (2013.01);
(Continued)

(58) Field of Classification Search
CPC . A61F 2/966; A61F 2/962; A61F 2/95; A61B 1/00154; A61B 1/00
See application file for complete search history.

(56) References Cited

U.S. PATENT DOCUMENTS

| | | | | |
|---|---|---|---|---|
| 2004/0215312 A1* | 10/2004 | Andreas | .................. | A61F 2/958 |
| | | | | 623/1.11 |
| 2005/0090889 A1* | 4/2005 | Yanuma | .................... | A61F 2/95 |
| | | | | 623/1.11 |
| 2006/0259124 A1* | 11/2006 | Matsuoka | ............... | A61F 2/966 |
| | | | | 623/1.12 |

FOREIGN PATENT DOCUMENTS

| | | |
|---|---|---|
| JP | 2004-181230 A | 7/2004 |
| JP | 2004-522525 A | 7/2004 |

(Continued)

OTHER PUBLICATIONS

International Search Report dated Apr. 14, 2020 received in PCT/JP2020/006690.

*Primary Examiner* — Jerrah Edwards
*Assistant Examiner* — Teresa M Dudden
(74) *Attorney, Agent, or Firm* — Scully, Scott, Murphy & Presser, P.C.

(57) ABSTRACT

The stent delivery system includes: an outer tube in which a first opening is formed in a distal end and a second opening is formed between the distal end and a proximal end; an inner tube inserted into the outer tube from the first opening to the second opening, and disposed outside of the outer tube from the second opening to the proximal end of the outer tube; and a stent stored between the inner tube and the outer tube. The outer tube and the inner tube are configured to be inserted into a channel of an endoscope. The second opening is formed at a position where the second opening is arranged inside the channel when a storage position is protruded from a distal end side of the channel.

19 Claims, 12 Drawing Sheets

(51) Int. Cl.
   *A61B 1/018* (2006.01)
   *A61F 2/962* (2013.01)
   *A61F 2/95* (2013.01)

(52) U.S. Cl.
   CPC .............. *A61B 1/018* (2013.01); *A61F 2/962*
   (2013.01); *A61B 1/00* (2013.01); *A61F 2/95*
   (2013.01)

(56) References Cited

FOREIGN PATENT DOCUMENTS

| | | | |
|---|---|---|---|
| JP | 2007-526096 | A | 9/2007 |
| JP | 2010-517735 | A | 5/2010 |
| JP | 2010-527694 | A | 8/2010 |
| KR | 10-1772489 | B1 | 8/2017 |
| WO | 2002/062266 | A2 | 8/2002 |
| WO | 2005/084382 | A2 | 9/2005 |
| WO | 2008/153765 | A2 | 12/2008 |
| WO | 2009/105089 | A2 | 8/2009 |
| WO | 2015/146288 | A1 | 10/2015 |

* cited by examiner

STENT DELIVERY SYSTEM, ENDOSCOPE SYSTEM, AND STENT INDWELLING METHOD

The present disclosure relates to a stent delivery system, an endoscope system, and a stent indwelling method. This application is a continuation application based on International Patent Application No. PCT/JP2020/006690 filed on Feb. 20, 2020, the contents of the PCT international application is incorporated herein by reference.

A procedure of indwelling a stent to expand stenosis or obstruction (hereinafter referred to as "stenosis, etc.") in the gastrointestinal tract is known. A stent delivery system is used to indwell a stent in a stenosis or the like. The stent delivery system transports a stent to a stenosis or the like through a treatment tool channel of an endoscope.

For example, in a conventional stent delivery system disclosed in Published Japanese Translation No. 2007-526096 of the PCT International Publication, a guide wire tube inserted through an inside of the sheath is provided so as to be slidable with respect to the sheath. The stent is housed in a gap between the guidewire tube and the sheath on a distal end part of the delivery system. The stent stored on the distal end part is indwelled in a stenosis or the like by pulling the sheath with respect to the guide wire tube toward a proximal side.

An operation of pulling the sheath with respect to the guide wire tube toward the proximal side is performed by an assistant who assists the endoscopes who operates the endoscope. The assistant pulls the sheath with respect to the guide wire tube toward the proximal side while fixing the guide wire tube so that the position of the guide wire tube does not move, thereby the stent is indwelled in the desired position.

In conventional stent delivery systems, when the sheath is retracted to the proximal side, for example, a guide wire tube moves to the distal side due to the reaction generated by the contact between the curved sheath and the guide wire tube of the endoscope. In this case, a stent is indwelled in a position deviated from the desired position. In order to suppress the occurrence of this phenomenon, a coordinated operation in which the endoscopes adjusts the position of the stent delivery system in accordance with the operation of pulling the sheath by the assistant is performed.

SUMMARY

A first aspect of the disclosure relates to a stent delivery system including: an outer tube in which a first opening is formed in a distal end and a second opening is formed between the distal end and a proximal end; an inner tube inserted into the outer tube from the first opening to the second opening and disposed outside of the outer tube from the second opening to the proximal end of the outer tube; and a stent stored between the inner tube and the outer tube. The outer tube and the inner tube are configured to be inserted into a channel of an endoscope. The second opening is formed at a position where the second opening is arranged inside the channel when a storage position is protruded from a distal end side of the channel.

A second aspect of the present disclosure relates to an endoscope system including a stent delivery system including an outer tube in which a first opening is formed in a distal end and a second opening is formed between the distal end and a proximal end; an inner tube inserted into the outer tube from the first opening to the second opening, and disposed outside of the outer tube from the second opening to the proximal end of the outer tube, and including a stent stored between the inner tube and the outer tube; and an endoscope having a channel into which the stent delivery system is insertable. The second opening is formed at a position where the second opening is arranged inside the channel when a storage position is protruded from a distal end side of the channel.

A third aspect of the present disclosure relates to a stent indwelling method using an endoscope and a stent delivery device including steps of: inserting the stent delivery system into a channel of the endoscope; inserting a distal end of the stent delivery system through the channel to an indwelling positon of a stent; fixing an inner tube of the stent delivery system to the endoscope after arriving the distal end of the stent delivery system at the indwelling positon; exposing the stent housed between the inner tube and an outer tube of the stent delivery system from the outer tube by pulling the outer tube toward a proximal side, the outer tube being provided in the stent delivery system so as to cover the inner tube.

DETAILED DESCRIPTION OF EXEMPLARY EMBODIMENTS

First Embodiment

The first embodiment of the present disclosure will be described with reference to FIGS. 1 to 6.

[Endoscope System 300]

Figure 1:
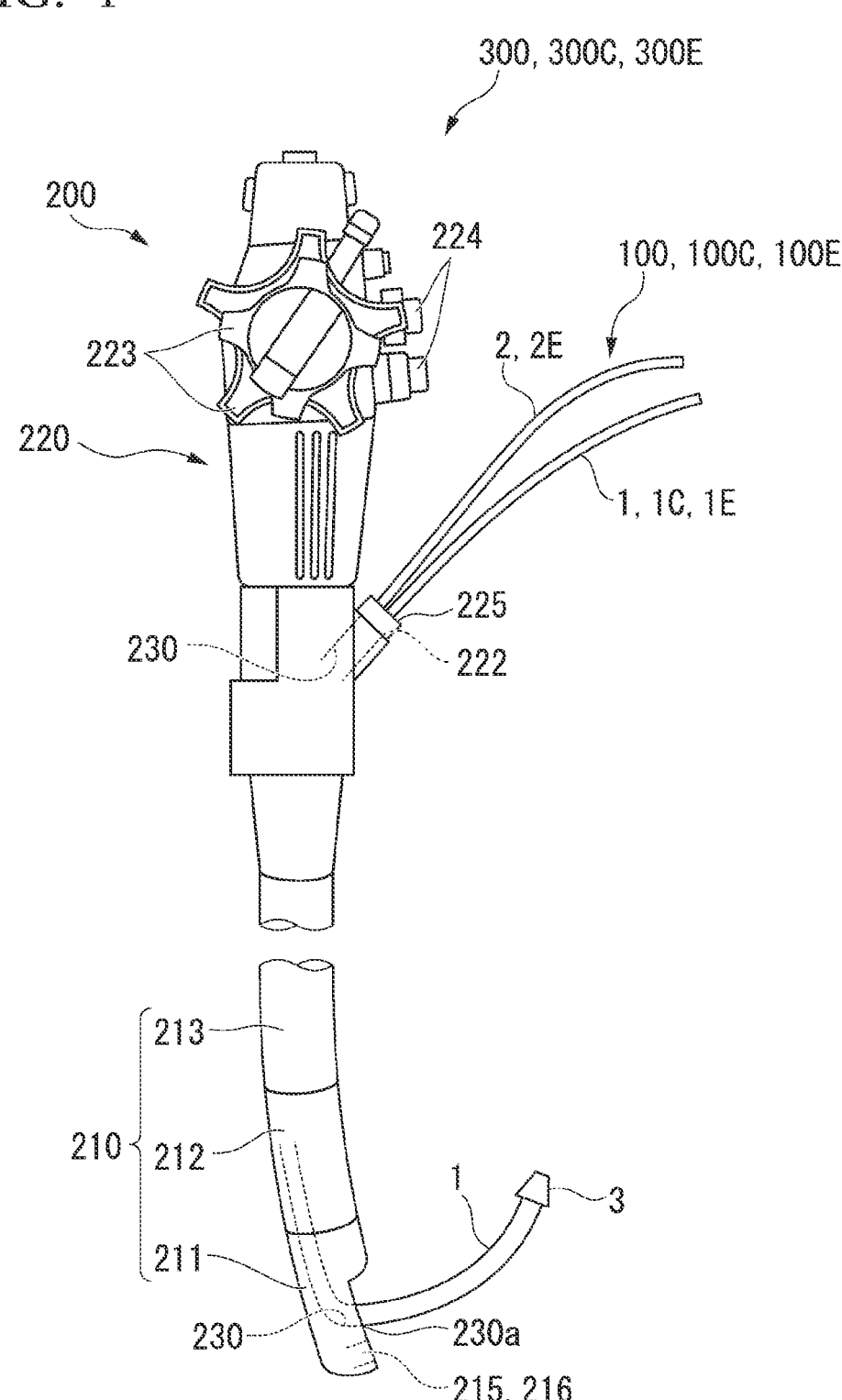
FIG. 1 is a view illustrating the overall configuration of an endoscope system according to the first Embodiment.

FIG. 1 is a view illustrating the overall configuration of an endoscope system 300 according to the first Embodiment.

The endoscope system 300 includes an endoscope 200 and a stent delivery system 100 inserted into the channel of the endoscope 200.

[Endoscope 200]

The endoscope 200 is a known side-view type flexible endoscope. The endoscope 200 has an elongated insertion portion 210 and an operation portion 220 provided at a proximal end portion of the insertion portion 210. The endoscope 200 may use a direct-view type flexible endoscope.

The insertion portion 210 includes a distal end hard portion 211 provided at the distal end portion thereof, a curved portion 212 attached to a proximal end side of the distal end hard portion 211 and configured to be bent by an operation, and a flexible tube portion 213 attached to a proximal end side of the curved portion 212. An image pickup unit 216 having a light guide 215 and a charge-coupled device (CCD) is provided on a side surface of the distal end hard portion 211 in a state exposing to an outside.

A treatment tool channel 230 for inserting an endoscopic treatment tool such as a stent delivery system 100 is formed in the insertion portion 210. A distal end part 230a of the treatment tool channel 230 is opened on a side surface of the distal end hard portion 211. A proximal end part of the treatment tool channel 230 extends to the operation portion 220.

The curved portion 212 is configured to be capable of being curved in the left-right direction and the upside-down direction. A distal end of the operation wire is fixed to a distal end side of the curved portion 212. The operation wire extends through the insertion portion 210 to the operation portion 220.

A knob 223 for operating the operation wire, and a switch 224 for operating the image pickup unit 216, or the like are provided on a proximal end side of the operation portion 220. The user is capable of bending the curved portion 212 in a desired direction by operating the knob 223.

A forceps port 222 communicating with the treatment tool channel 230 is provided on a distal end side of the operation portion 220. The user can insert an endoscopic treatment tool such as the stent delivery system 100 from the forceps port 222. A forceps plug 225 preventing humor from leaking is attached to the forceps port 222.

[Stent Delivery System 100]

Figure 2:
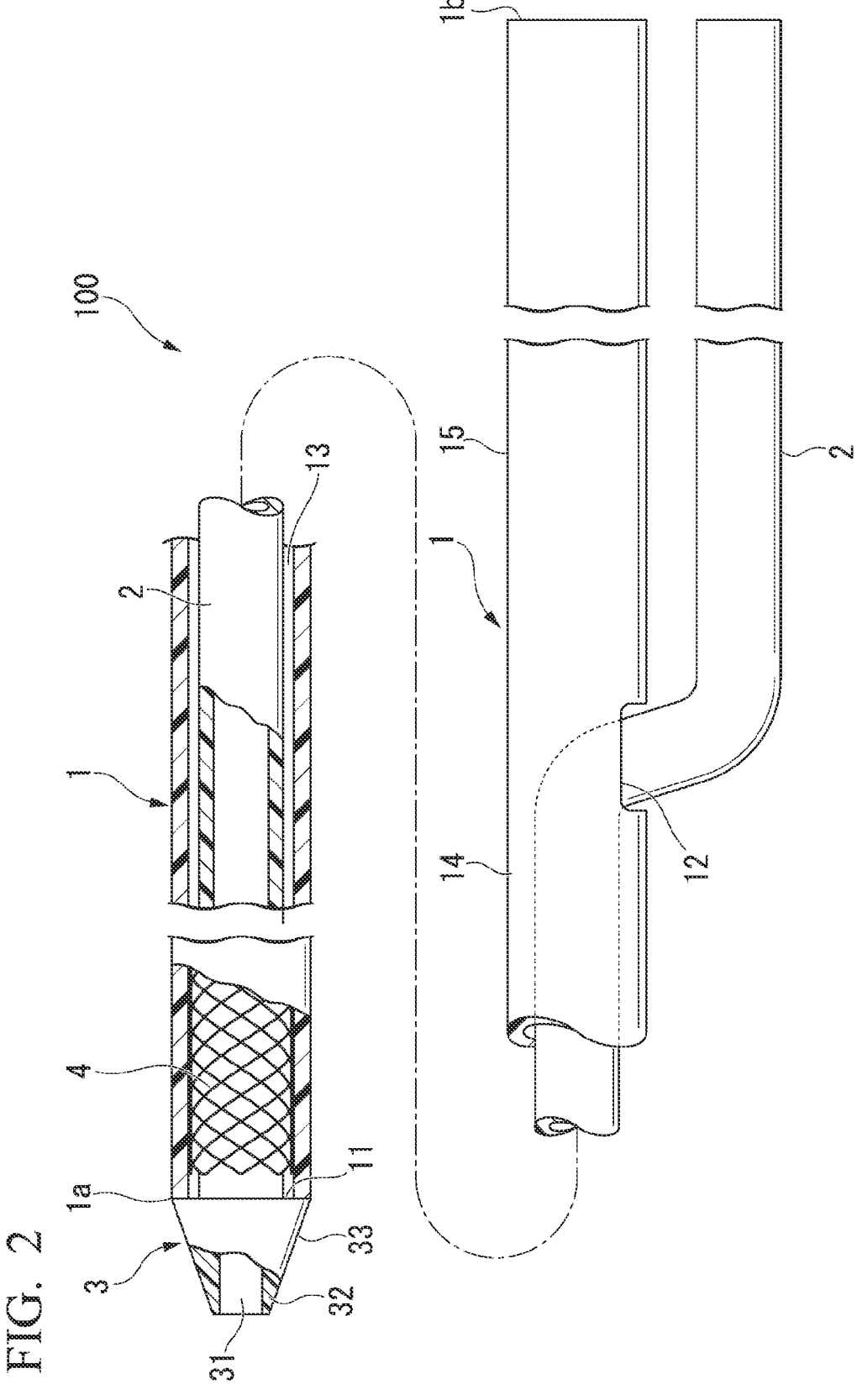
FIG. 2 is a cross-sectional and a partial interrupted view illustrating the stent delivery system of the endoscope system.

FIG. 2 is a cross-sectional and a partial interrupted view illustrating the stent delivery system. The stent delivery system 100 is formed in an elongated shape as a whole. The stent delivery system 100 includes an outer tube 1, an inner tube 2, a tip 3, and a stent 4.

Figure 3:
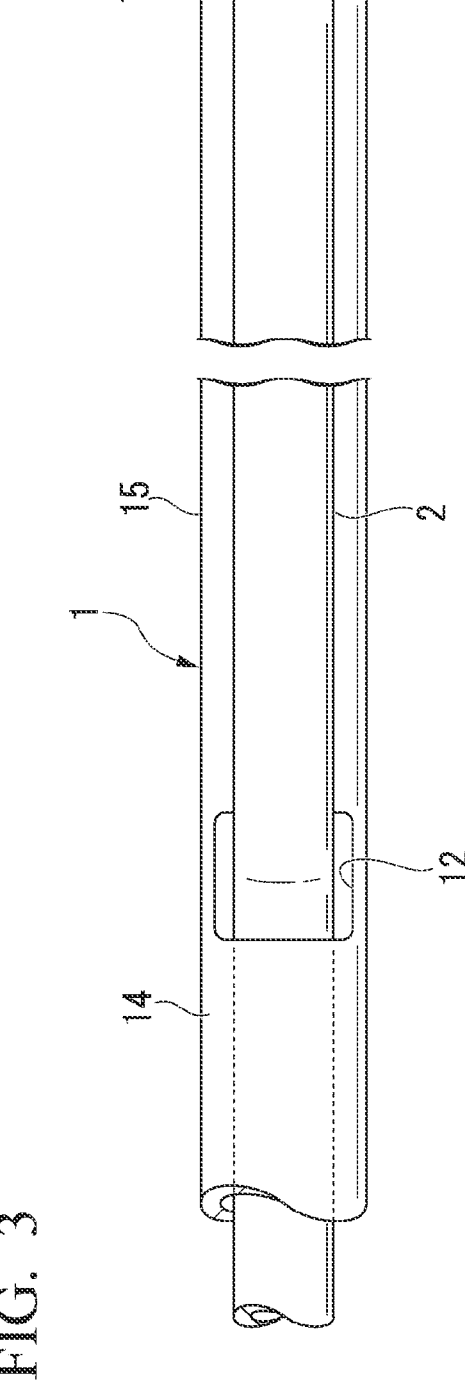
FIG. 3 is a view illustrating a second opening of an outer tube of the stent delivery system.

FIG. 3 is a view illustrating a second opening 12 of the outer tube 1. The outer tube 1 is an elongated tubular member insertable into the treatment tool channel 230 of the endoscope 200. The outer tube 1 is made of resin or the like and has flexibility. In the outer tube 1, a first opening 11 is opened at a distal end 1a and a second opening 12 is opened in a side surface between the distal end 1a and a proximal end 1b of the outer tube 1. The first opening 11 and the second opening 12 communicate with the internal space (lumen) 13 of the outer tube 1. The first opening 11 and the second opening 12 are substantially circular openings through which the inner tube 2 is insertable.

Figure 4:
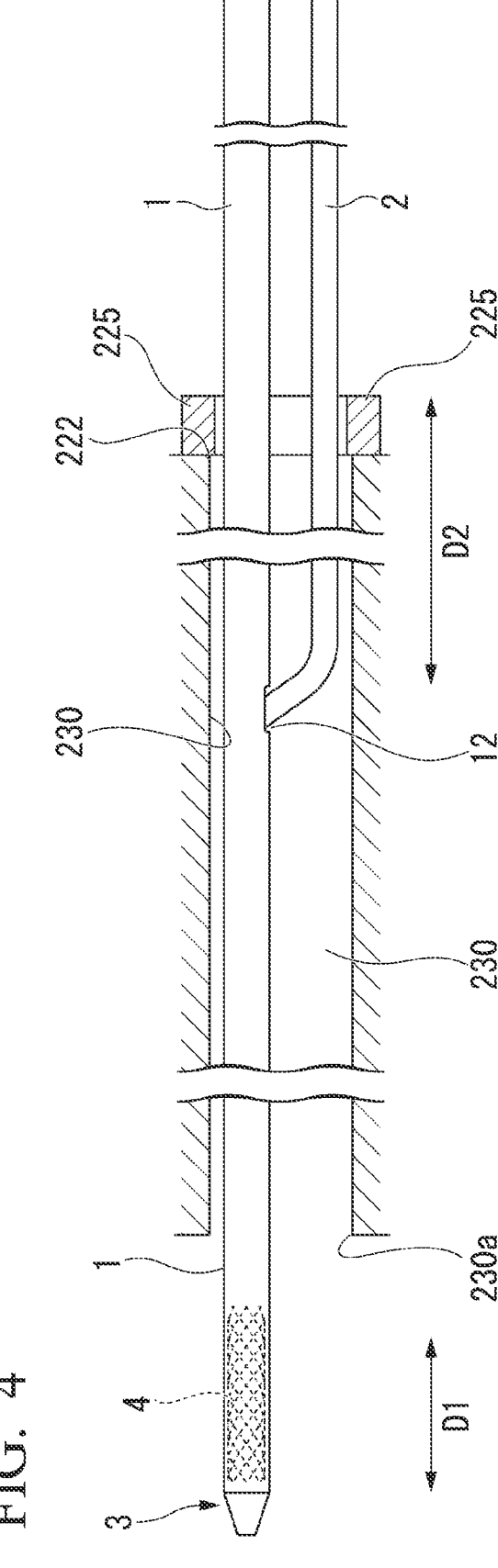
FIG. 4 is a view illustrating the stent delivery system inserted into a treatment instrument channel of the endoscope of an endoscope.

FIG. 4 is a view illustrating the stent delivery system 100 inserted into the treatment instrument channel 230. A distal end of the stent delivery system 100 shown in FIG. 4 protrudes from a distal end part 230a of the treatment tool channel 230 of the endoscope 200. In a state where the stent 4 storage location of the stent delivery system 100 is projected from the distal end 230a of the treatment tool channel 230 of the endoscope 200 and the stent 4 is located at the indwelling position, the second opening 12 is formed to be located inside the treatment tool channel 230. In this state, the length D2 from the second opening 12 to the forceps plug 225 is longer than the longitudinal length D1 of the stent 4.

Figure 5:
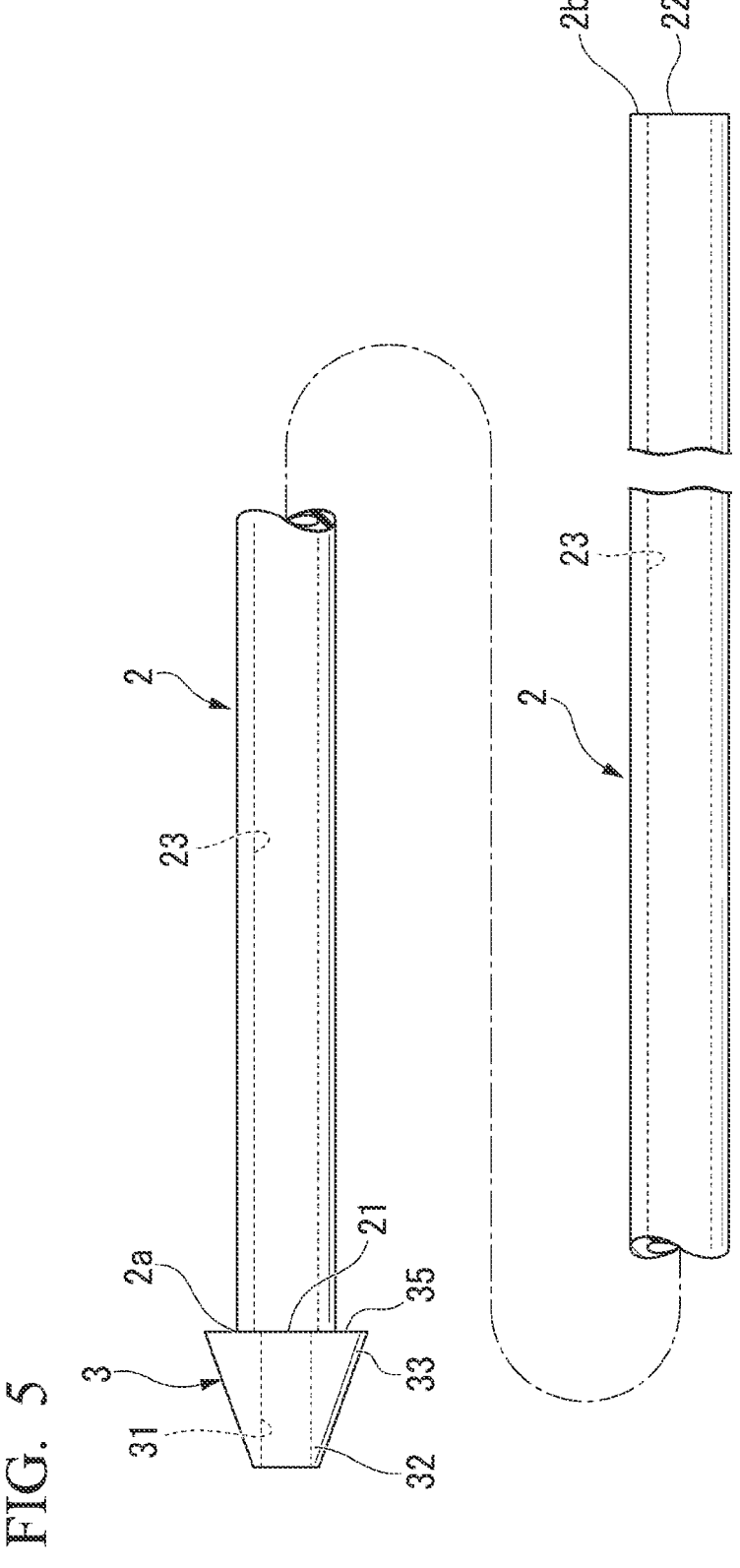
FIG. 5 is a view illustrating the overall configuration of the inner tube and a chip of the stent delivery system.

FIG. 5 a view illustrating the overall configuration of the inner tube 2 and the chip 3. The inner tube 2 is an elongated tubular member insertable into the treatment tool channel 230 of the endoscope 200. The inner tube 2 is made of resin or the like and has flexibility. In the inner tube 2, a distal end opening 21 is opened at a distal end 2a and a proximal opening 22 is opened at a proximal end 2b. The distal end opening 21 and the proximal opening 22 communicate with the lumen (guide wire lumen) 23 of the inner tube 2.

As shown in FIG. 2, the inner tube 2 passes through the first opening 11 and the second opening 12 and is inserted into the lumen 13 of the outer tube 1 so as to be movable relative to the outer tube 1. The outer diameter of the inner tube 2 inserted through the lumen 13 of the outer tube 1 is smaller than the inner diameter of the lumen 13 of the outer tube 1. The inner tube 2 is disposed outside of the outer tube 1 from the second opening 12 to the proximal end 1b of the outer tube. That is, the outer tube 1 and the inner tube 2 are parallel to each other between the second opening 12 and the distal end 1b of the outer tube 1.

Here, in the outer tube 1, a distal end 1a side portion from the second opening 12 is called a first outer tube (first member) 14, and a proximal end 1b side from the second opening 12 is called a second outer tube (second member) 15. Though the first outer tube 14 is necessary to have a lumen 13 for inserting the inner tube 2, the second outer tube 15 is not necessary to have the lumen 13 for inserting the inner tube 2. A reinforcing member may be loaded into the lumen 13 of the second outer tube 15. The reinforcing member is made by, for example, Ni—Ti based alloy, stainless steel (SUS), and Co—Cr based alloy, or the like. As a result of the reinforcing member, in the whole of the stent delivery system 100, a rigidity of the proximal end side is higher than a rigidity of the distal end side, thereby an operation of the stent delivery system 100 at the proximal side becomes easily performed.

The second outer tube 15 may be an elongated member and formed individually from the first outer tube 14 and may be formed such that a distal end of the second outer tube 15 is connected the first outer tube 14. The second outer tube 15 may be a wire or a rod formed of, for example, metals (Ni—Ti alloy, Stainless Steel (SUS), Co—Cr alloy), or resins. For example, an outer diameter of the second outer tube 15 may be formed to be smaller than an outer diameter of the first outer tube 14, thereby a proximal side of the stent delivery system 100 becomes thinner.

As shown in FIG. 5, the chip 3 has a substantially conical shape and has a through hole 31 extending in the axial direction. The tip 3 has a distal end 32 and a proximal end 33 and is connected to the inner tube 2 on the proximal end 33 side. The distal end 32 has a diameter smaller than a diameter of the proximal end 33. Since the diameter of the proximal end 33 is larger than the outer diameter of the inner tube 2, there is a step 35 at a connection portion between the tip 3 and the inner tube 2. Since the through hole 31 communicates with the lumen 23 of the inner tube 2 via the distal end opening 21, the guide wire is entered into the guide wire lumen 23 of the inner tube 2 when the guide wire is inserted into the through hole 31 of the tip 3.

The stent 4 is a tubular self-expanding stent. The stent 4 is formed by weaving a wire. The stent 4 is housed in a gap between the outer tube 1 and the inner tube 2 at a position more distal side than the second opening 12 in a state where the inner tube 2 is passed through the inside of the stent 4 and the diameter of the stent is reduced. The stent 4 is locked to a locking portion (not shown) formed on the outer peripheral surface of the inner tube 2. Accordingly, the stent 4 is positioned with respect to the inner tube 2 in the reduced diameter state and does not move relative to the inner tube 2 in the longitudinal direction. The stent 4 may use a laser-cut type stent formed by cutting a metal cylinder by a laser.

The materials of the outer tube 1 and the inner tube 2 are not particularly limited as long as the desired mechanical properties are satisfied in the outer tube 1 and the inner tube 2. As the material of the outer tube 1 and the inner tube 2, the following materials can be exemplified. Olefin resins such as polypropylene and polyethylene, and their copolymer resins, polyester resins such as polyethylene terephthalate (PET) and polybutylene terephthalate (PBT), and general-purpose resins such as polyvinyl alcohol (PVA). Engineering resins such as polyamide resins, fluororesins (e.g, polytetrafluoroethylene (PTFE), polyvinylidene fluoride (PVDF), PFA, FEP, ETFE, etc.), polyetheretherketone (PEEK, etc.). Various elastomer resins (polystyrene-based, polyolefin-based, polyurethane-based, polyester-based, polyamide-based, polyvinyl chloride-based, etc.), silicone-containing resins, polyurethane-based resins, etc. may be used alone or in combination. Further, in order to suppress the occurrence of buckling and the like, a material composite with a mesh made of stainless steel or the like may also be used. For stent delivery systems used under X-ray fluoroscopy, X-ray opaque metallic markers (medical X-ray opaque metals and alloys such as platinum, tungsten, and iridium) may be added or X-ray opaque, and various materials (such as barium sulfate) may be mixed.

The wire forming the stent 4 is a superelastic alloy containing Ni—Ti as the main material. The superelastic alloy containing Ni—Ti as the main material is not permanently deformed at the time of weaving, and the weaving shape is memorized by applying heat treatment in the weaved state.

A stent indwelling method using the endoscope system 300 including the stent delivery system 100 configured as described above will be described with an exemplary example of a procedure for placing a stent 4 in a bile duct.

The endoscopes inserts the insertion portion 210 of the endoscope 200 into the body cavity of the patient through a natural opening such as the mouth. At that time, the endoscopes operates the knob 223 or the like to bend the curved portion 212 as necessary.

The endoscopes passes the guide wire G through the treatment tool channel 230 of the endoscope 200 and inserts the guide wire G into the bile duct while observing with the endoscope 200. Subsequently, the endoscopes operates the guide wire G under fluoroscopy to pass through the stenosis site in the bile duct and move the distal end of the guide wire G closer to the liver than the stenosis site (desired position).

The endoscopes inserts the proximal end of the guide wire G protruding from the forceps plug 225 of the endoscope 200 into the through hole 31 of the tip 3 of the stent delivery system 100. The guide wire G enters the guide wire lumen 23 of the inner tube 2 through the through hole 31.

The endoscopes advances the stent delivery system 100 along the guide wire G by pushing the stent delivery system 100 while holding the guide wire G (insertion step). The distal end of the stent delivery system 100 projects from the distal end 230a of the treatment tool channel 230 of the endoscope 200. When the distal end of the stent delivery system 100 passes through the stenosis site (target position), the endoscopes advances and retreats the stent delivery system 100 to determine the indwelling position of the stent 4. The endoscopes may insert the stent delivery system 100 into the treatment tool channel 230 without using the guide wire G.

As shown in FIG. 4, in a state where the stent 4 storage location of the stent delivery system 100 is projected from the distal end 230a of the treatment tool channel 230 of the endoscope 200 and the stent 4 is located in the indwelling position, the second opening 12 is located inside the treatment tool channel 230. In the state, the inner tube 2 and the outer tube 1 are individually exposed out from the forceps plug 225.

Figure 6:
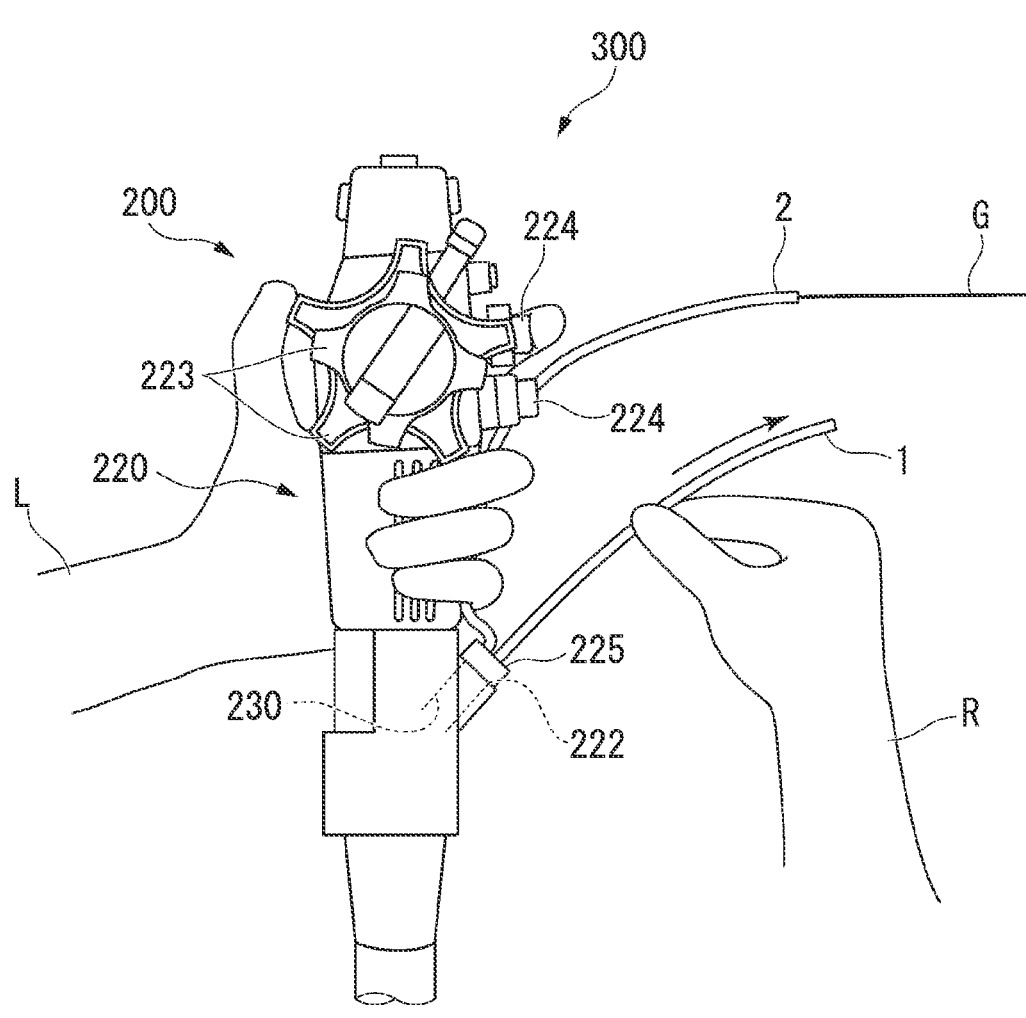
FIG. 6 is a view describing the operation of an endoscopes when indwelling a stent having the stent delivery system into an indwelling position.

FIG. 6 is a view describing the operation of an endoscopes when indwelling the stent 4 into a target position. After determining the target position of the stent 4, the endoscopes fixes the inner tube 2 to the vicinity of the forceps plug 225 of the operation portion 220 with the other hand L which holding the operation portion 220 of the endoscope 200 (fixing step), in this state, the endoscopes pulls the outer tube 1 toward the proximal side with the hand R (traction step). Then, the outer tube 1 retracts with respect to the inner tube 2. As a result, the stent 4 is gradually exposed from the distal end side thereof and expands. The endoscopes can perform the procedure of indwelling the stent 4 while operating the endoscope 200 without the assistance of an assistant.

The endoscopes pulls the outer tube 1 toward the proximal side while fixing the inner tube 2 to the operation portion 220, so that only the outer tube 1 retracts to the proximal side without retracting and advancing the inner tube 2. The outer tube 1 is less likely to contact with the inner tube 2 when the outer tube 1 is pulled toward the proximal side. As the result, the reaction force generated by the contact and making the inner tube 2 move the distal side is less likely to occur. Therefore, the position of the inner tube 2 is maintained, and the position in which the stent 4 is housed is unlikely to deviate from the target position.

A length D2 form the second opening 12 to the forceps plug 225 is, as shown in FIG. 4, longer than the longitudinal length D1 of the stent 4. Therefore, when the endoscopes pulls the outer tube 1 toward the proximal side while fixing the inner tube 2 to the operation unit 220, the second opening 12 is not exposed out from the forceps plug 225. Since the inner tube 2 is exposed from the outer tube 1, the vicinity of the second opening 12 of the outer tube 1, where is the largest outer diameter in the delivery system 100, is difficult to come into contact with the forceps opening 222 and the forceps plug 225. As the result, when the outer tube 1 is pulled toward the proximal side, a reaction force that makes the inner tube 2 advance and retract is unlikely to occur.

When the stent 4 is completely exposed, the stent 4 expands radially at the entire area of the axial direction, and the inner diameter of the stent 4 becomes larger than the outer diameter of the inner tube 2. Accordingly, the lock between the stent 4 and the inner tube 2 is also released.

In a state before the stent 4 is completely expanded, the stent 4 can be housed again (recapture) between the outer tube 1 and the inner tube 2 by advancing the outer tube 1 with respect to the inner tube 2 and reduces the diameter of the stent 4. Recapture is useful when resetting the indwelling position.

When the endoscopes retracts the inner tube 2 after the locking between the stent 4 and the inner tube 2 is released, the stent 4 stays in the indwelling position and the inner tube 2 is removed from the stent 4.

When the endoscopes pulls out the stent delivery system 100 excluding the stent 4, the indwelling procedure of the stent 4 is completed. Then, a contrast tube may be introduced along the guide wire and a contrast agent may be used to confirm the open state of the stenosis.

According to the stent indwelling method using the endoscope system 300 including the stent delivery system 100 according to the present embodiment, the endoscopes can easily indwell the stent 4 at a target position without the assistance of the assistant. Since the inner tube 2 and the outer tube 1 are individually exposed out from the forceps plug 225, the endoscopes can fix the inner tube 2 to the operation portion 220 and can retract only the outer tube 1 toward the proximal side. When the endoscopes pulls the outer tube 1 toward the proximal side, the outer tube 1 and the inner tube 2 hardly contact with each other. As the result, the reaction force that is generated by the contact and makes the inner tube 2 advance and retract hardly occurs. Therefore, the position of the inner tube 2 is maintained, and the position in which the stent 4 is housed is unlikely to deviate from the target position.

Although the first embodiment has been described in detail with reference to the drawings, the specific configuration is not limited to the embodiment and includes design changes and the like within a range not deviating from the gist of the present invention. The components shown in the above-described embodiment and the modifications shown below can be appropriately combined and configured.

Modified Example 1

Figure 7:
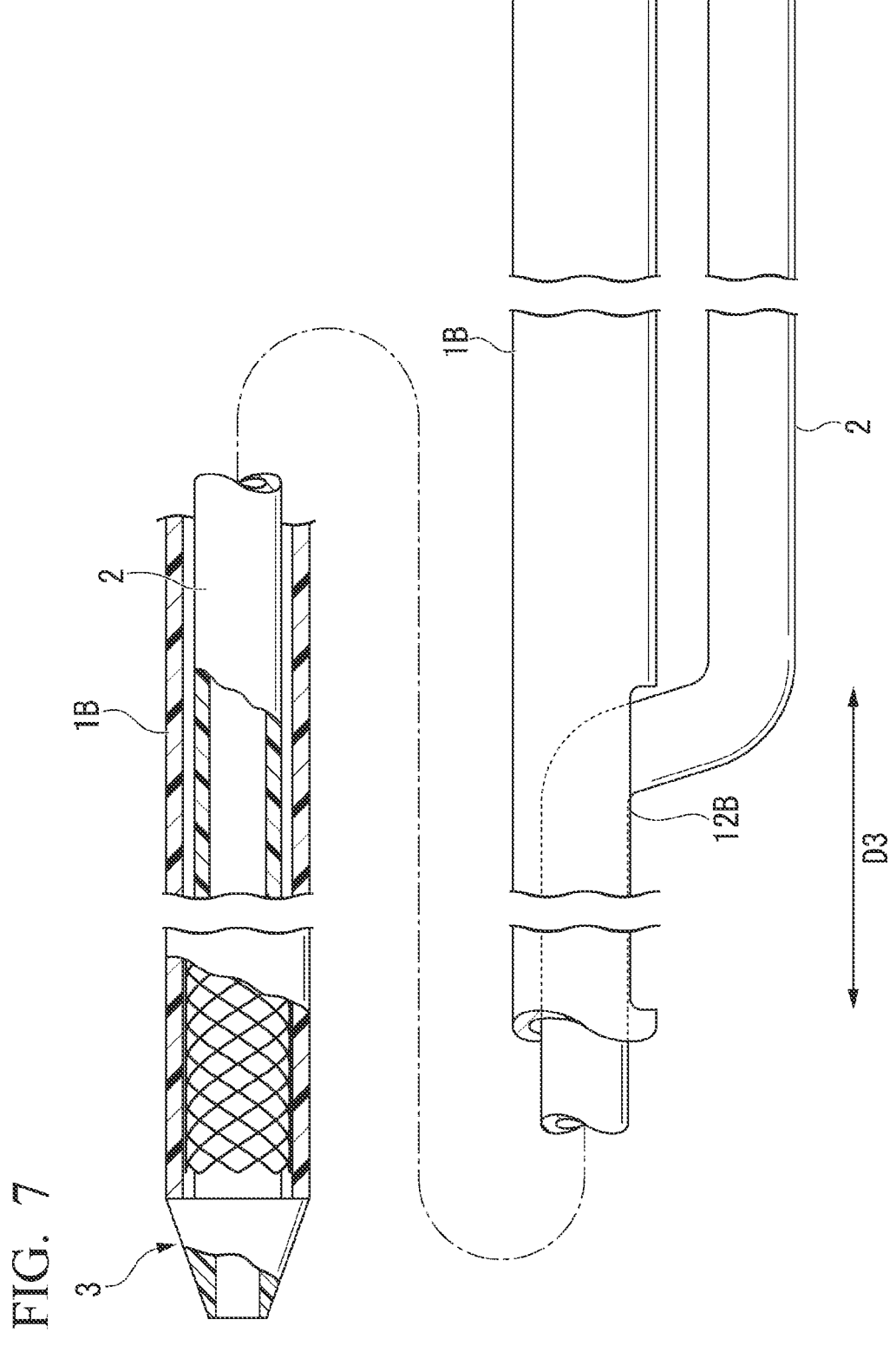
FIG. 7 is a view illustrating a modified example of a second opening in the outer tube of the stent delivery system according to the embodiment.

For example, in the above-described embodiment, the second opening 12 is a substantially circular opening through which the inner tube 2 is configured to be inserted, but the second opening is not limited to the example. FIG. 7 is view illustrating a modified example of the stent delivery system 1B including the outer tube 1B which has a second opening 12B as the modified example of the second opening 12. The second opening 12B is formed at a lateral surface of the outer tube 1B between the distal end 1a and the proximal end 1b. The second opening 12B is communicated with the lumen 13 of the outer tube 1B. The second opening 12B is an opening through which the inner tube 2 is inserted and is an elongated hole formed along the longitudinal direction. The longitudinal length D3 of the second opening 12B is longer than the longitudinal length D1 of the stent 4. When the endoscopes pulls the outer tube 1 toward the proximal side, the outer tube 1 and the inner tube 2 are less likely to contact with each other at the vicinity of the second opening 12B. As the result, the reaction force that is generated by the contact and makes the inner tube 2 move toward the distal side hardly occurs. Therefore, the position of the inner tube 2 is maintained, and the position in which the stent 4 is housed is unlikely to deviate from the target position.

Second Embodiment

The second embodiment of the present disclosure will be described with reference to FIG. 8. In the following description, the same constituent elements as those already described in the first embodiment are designated by the same reference signs, and duplicate descriptions thereof will be omitted. In the endoscope system 300C according to the second embodiment, the second opening of the stent delivery system is different from the endoscope system 300 according to the first embodiment.

The endoscope system 300C includes the endoscope 200 and the stent delivery system 100C inserted into the channel of the endoscope 200.

Figure 8:
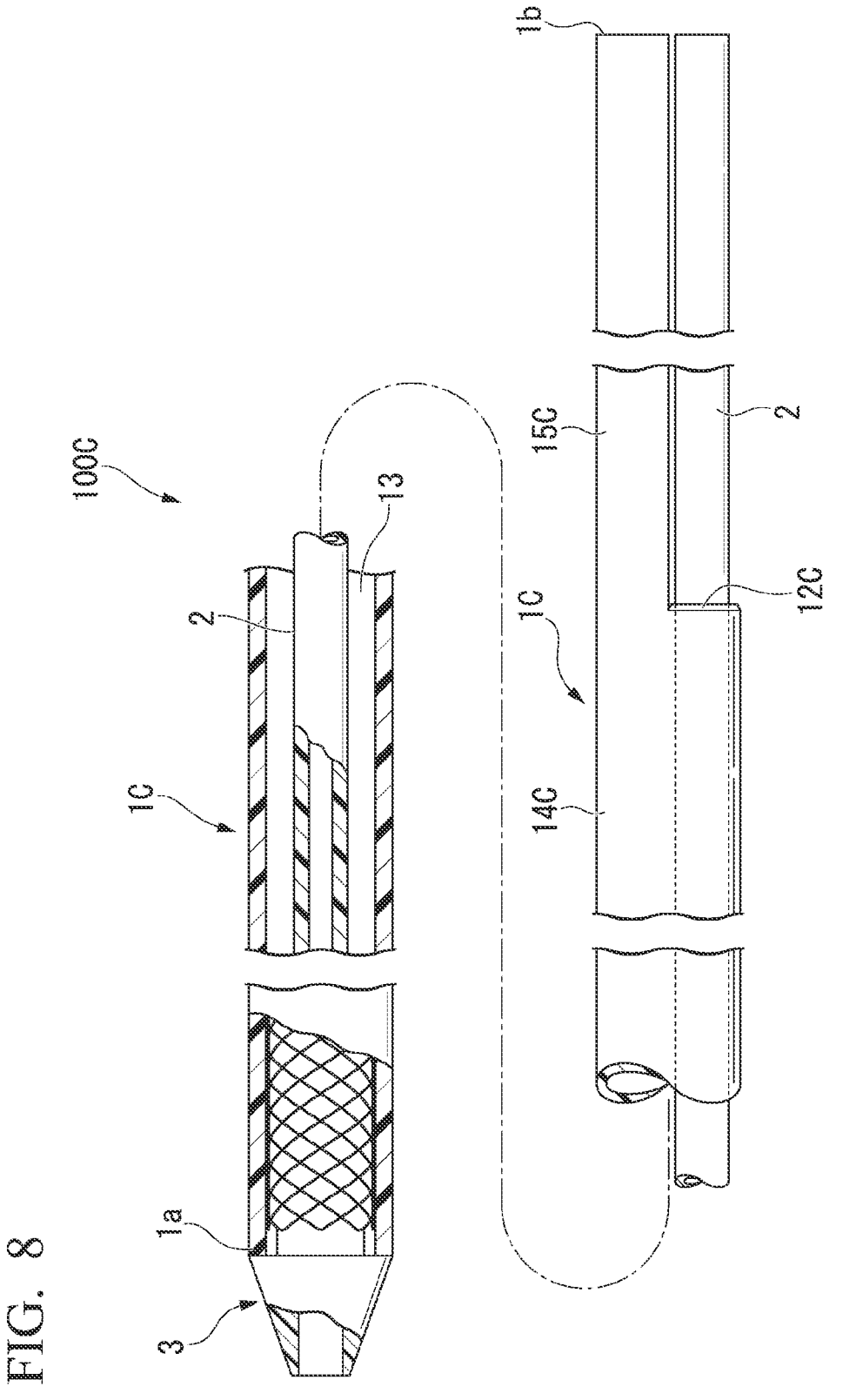
FIG. 8 is a cross-sectional and a partial interrupted view illustrating the stent delivery system of the endoscope system of the second embodiment.

FIG. 8 is a cross-sectional and a partial interrupted view illustrating the stent delivery system 100C of the second embodiment. The stent delivery system 100C includes the outer tube 1C, the inner tube 2, the tip 3, and the stent 4.

The outer tube 1C is an elongated tubular member insertable into the treatment tool channel 230 of the endoscope 200. The outer tube 1C is made of resin or the like and has flexibility. In the outer tube 1C, a first opening 11 is opened at the distal end 1a and a second opening 12C is opened between the distal end 1a and the proximal end 1b.

As shown in FIG. 8, the inner tube 2 passes through the first opening 11 and the second opening 12C and is inserted into the lumen 13 of the outer tube 1 so as to be relatively movable.

Here, in the outer tube 1C, the distal end 1a side portion from the second opening 12C is called the first outer tube (first member) 14C, and the proximal end 1b side from the second opening 12C is called a second outer tube (second member) 15C. The outer diameter of the first outer tube 14C is larger than the outer diameter of the second outer tube 15C. A reinforcing member may be loaded into the lumen 13 of the second outer tube 15C. In the whole of the stent delivery system 100C, a rigidity of the proximal end side is higher than a rigidity of the distal end side, thereby an operation of the stent delivery system 100C at the proximal side becomes easily performed.

The second opening 12C is opened at the distal end 1b side of the outer tube 1C in the longitudinal direction. An opening surface of the second opening 12C is perpendicular to the longitudinal direction of the outer tube 1C. Therefore, in the inner tube 2, a portion passing through the second opening 12C does not curve. When the endoscopes pulls the outer tube 1C toward the proximal side, the outer tube 1C and the second tube 2 hardly contact with each other around the second opening 12C.

According to the stent indwelling method using the endoscope system 300C including the stent delivery system 100C according to the present embodiment, the endoscopes easily indwells the stent 4 at a target position such as stenosis without the assistance of an assistant. Since the inner tube 2 and the outer tube 1C are individually exposed out from the forceps plug 225, the endoscopes can fix the inner tube 2 to the operation portion 220 and can retract only the outer tube 1C toward the proximal side. When the endoscopes pulls the outer tube 1C toward the proximal side, the outer tube 1C and the inner tube 2 hardly contact with each other. As the result, the reaction force that is generated by the contact and makes the inner tube 2 advance and retract hardly occurs. Therefore, the position of the inner tube 2 is maintained, and the position in which the stent 4 is housed is unlikely to deviate from the target position.

Although the second embodiment of the present disclosure has been described in detail with reference to the drawings, the specific configuration is not limited to this embodiment and includes design changes and the like within a range not deviating from the gist of the present invention. The components shown in the above-described embodiments and modifications can be appropriately combined and configured.

Modified Example 2

Figure 9:
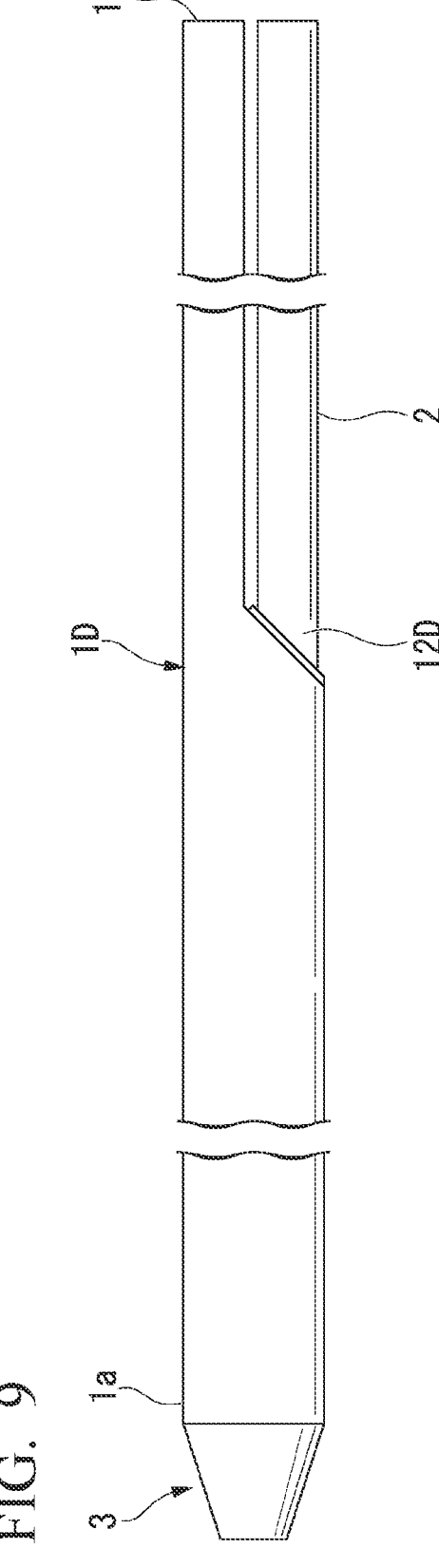
FIG. 9 is a view illustrating a modified example of a second opening in the outer tube of the stent delivery system according to the embodiment.

For example, in the above described embodiment, the second opening 12C is opened at the distal end 1b side of the outer tube 1C in the longitudinal direction, but the second opening is not limited to the example. FIG. 9 is view illustrating a modified example of the stent delivery system 1D including the outer tube 1D which has a second opening 12D as the modified example of the second opening 12C. The second opening 12D is formed in the outer tube 1D between the distal end 1a and the proximal end 1b. The second opening 12D is communicated with the lumen 13 of the outer tube 1D. The second opening 12D is opened to a direction inclined with respect to the longitudinal direction of the outer tube 1D. An opening surface of the second opening 12D is inclined to the longitudinal direction of the outer tube 1D. In the inner tube 2, a portion passing through the second opening 12D does not curve. Since an opening cross section area of the second opening 12D is larger in comparison with the opening cross section area of the second opening 12C, the outer tube 1D and the inner tube 2 hardly contact with each other around the second opening 12D. As the result, the reaction force that is generated by the contact and makes the inner tube 2 move toward the distal side hardly occurs.

Third Embodiment

The third embodiment of the present disclosure will be described with reference to FIG. 10. In the following description, the same constituent elements as those already described in the first embodiment are designated by the same reference signs, and duplicate description will be omitted. In the endoscope system 300E according to the third embodiment, an insertion route or the like of the guide wire of the stent delivery system is different from the endoscope system 300 according to the first embodiment.

The endoscope system 300E includes the endoscope 200 and the stent delivery system 100E inserted through the channel of the endoscope 200.

Figure 10:
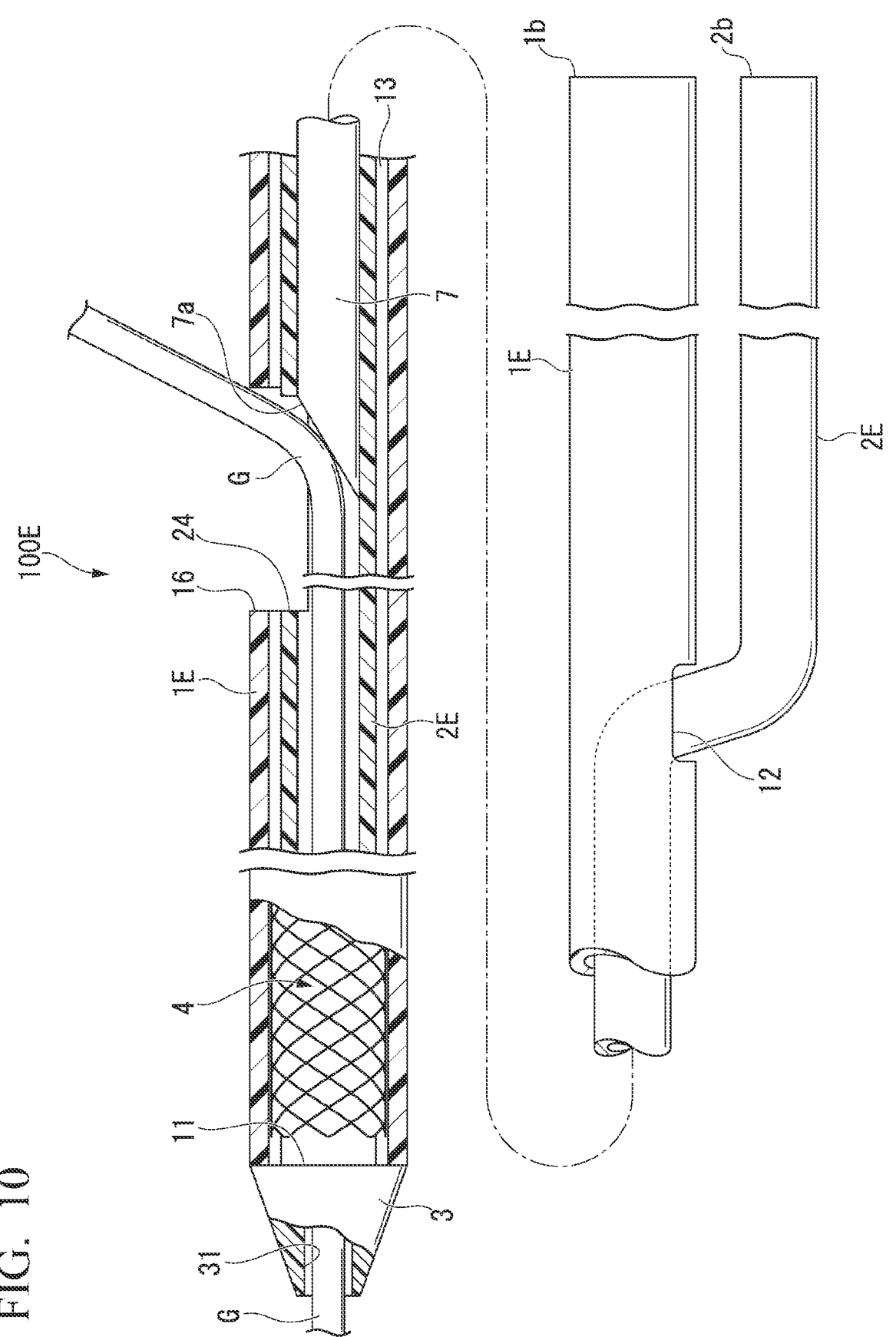
FIG. 10 is a cross-sectional and a partial interrupted view illustrating the stent delivery system of the endoscope system according to the third embodiment.

FIG. 10 is a cross-sectional and a partial interrupted view illustrating the stent delivery system 100E. The stent delivery system 100E includes the outer tube 1E, the inner tube 2E, the tip 3, and the stent 4.

The outer tube 1E is an elongated tubular member insertable into the treatment tool channel 230 of the endoscope 200. The outer tube 1E is made of resin or the like and has flexibility. In the outer tube 1E, the first opening 11 is opened at the distal end 1a, the second opening 12 is opened between the distal end 1a and the proximal end 1b, and a third opening 16 is opened in a lateral surface between the first opening 11 and the second opening 12. The third opening 16 communicates with an inner space (lumen) 13 of the outer tube 1. The outer tube 16 is an opening through which the guide wire is insertable.

The inner tube 2E is an elongated tubular member insertable into the treatment tool channel 230 of the endoscope 200. The inner tube 2E is made of resin or the like and has flexibility. In the inner tube 2E, a distal opening 21 is opened at a distal end 2a, an intermediate opening 24 is opened between the distal end 2a and the proximal end 2b. The distal opening 21 and the intermediate opening 24 communicate with the lumen (guide wire lumen) 23 of the inner tube 2.

As shown in FIG. 10, the guide wire G inserted through the through hole 31 of the tip 3 passes through the intermediate opening 24 and the third opening 16 and is pulled out of the stent delivery system 100. By pulling out the guide wire G from the intermediate portion of the stent delivery system 100, the guide wire G can be shortened, and the guide wire G is easily introduced into the treatment tool channel 230 of the stent delivery system 100.

As shown in FIG. 10, the inner tube 2E has a guide member 7 on the proximal end 2b side from the intermediate opening 24. The guide member 7 has an inclined surface 7a on the distal end 2a side. The inclined surface 7a guides the guide wire G so that the guide wire G passes through the intermediate opening 24.

In the inner tube 2E, the guide wire lumen 23 is not necessary on the proximal end 2b side from the guide member 7. A reinforcing member may be loaded into the guide wire lumen 23 at the proximal end 2b side from the guide wire member 7. The reinforcing member is made by, for example, Ni—Ti based alloy, stainless steel (SUS), and Co—Cr based alloy, or the like. In the whole of the stent delivery system 100E, a rigidity of the proximal end side is higher than a rigidity of the distal end side, thereby an operation of the stent delivery system 100E at the proximal side becomes easily performed.

The inner tube 2E is not necessary to extend to the proximal end side on the proximal end 2b side from the guide member 7, and an elongated member formed separately from the inner tube 2E and other than the tubular shape may be joined to the inner tube 2E. The elongated member is, for example, a wire or a rod made of a metal (Ni—Ti based alloy, SUS, Co—Cr based alloy) or a resin.

According to the stent indwelling method using the endoscope system 300E including the stent delivery system 100E according to the present embodiment, the endoscopes easily indwells the stent 4 at a target position such as stenosis without the assistance of the assistant. The position of the inner tube 2 can be maintained, and the position where the stent 4 is housed is unlikely to deviate from the target position.

Although the third embodiment of the present disclosure has been described in detail with reference to the drawings, the specific configuration is not limited to this embodiment and includes design changes and the like within a range not deviating from the gist of the present invention. The components shown in the above-described embodiments and modifications can be appropriately combined and configured.

Modified Example 4

Figure 11:
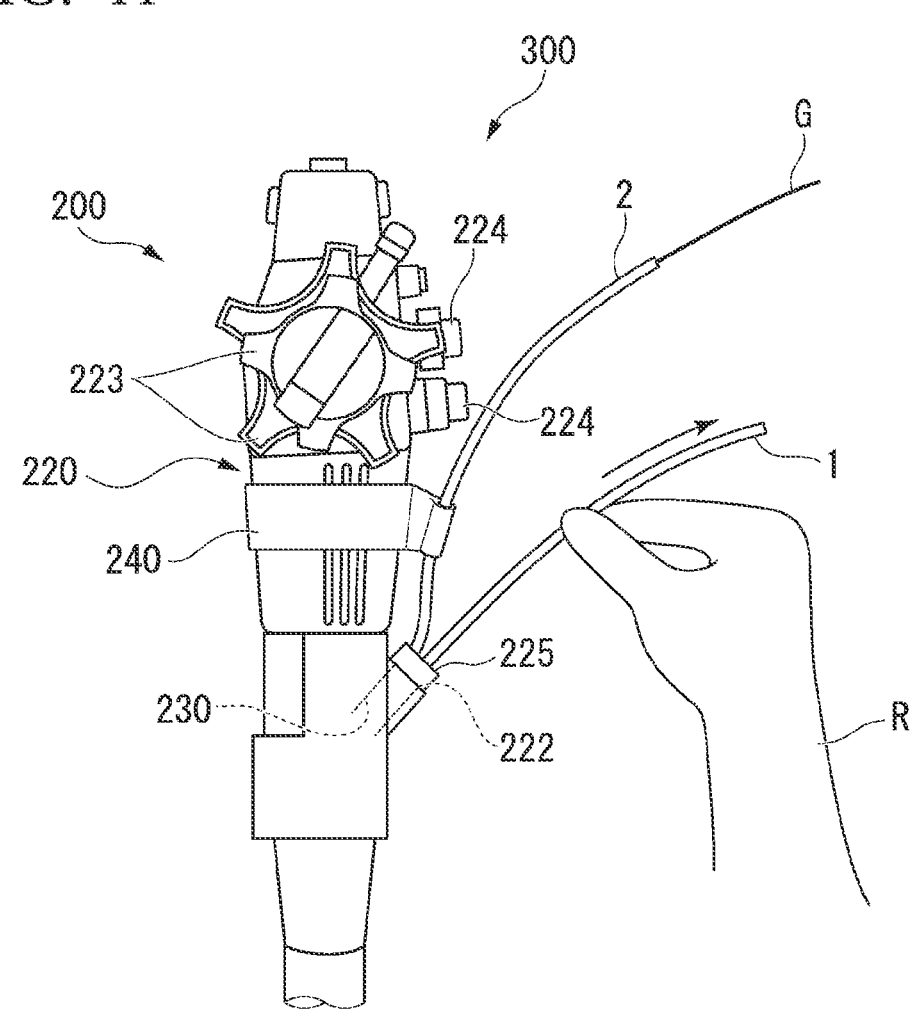
FIG. 11 is a view illustrating the endoscope of a modified example of the embodiment.

For example, in the above embodiment, although the endoscopes holds the inner tube 2 in the vicinity of the forceps plug 225 of the operation portion 220 by using one hand L holding the operation portion 220 of the endoscope 200, the fixing mode of the inner tube 2 is not limited to this. As shown in FIG. 11, the endoscope 200 may further include a fixing member 240. The fixing member 240 is attached in the vicinity of the operation portion 220, and the inner tube 2 can be fixed so that the relative positions of the inner tube 2 and the operation portion 220 do not change. Due to usage of the fixing member 240, the endoscopes does not need to fix the inner tube 2 with one hand L and can concentrate on the operation of the outer tube 1.

Modified Example 5

For example, in the above embodiment, the stent 4 is a self-expandable stent, but the stent is not limited to the self-expandable stent. The stent may be a non-self-expandable stent, and examples thereof include a Co—Cr based alloy stent and a biodegradable stent made of polylactic acid, polyglycolic acid, and a copolymer thereof. Further, the stent may be a stent that expands with a fluid. For example, the stent may be a non-self-expandable stent that is expanded by another treatment tool such as a balloon.

Modified Example 6

Figure 12:
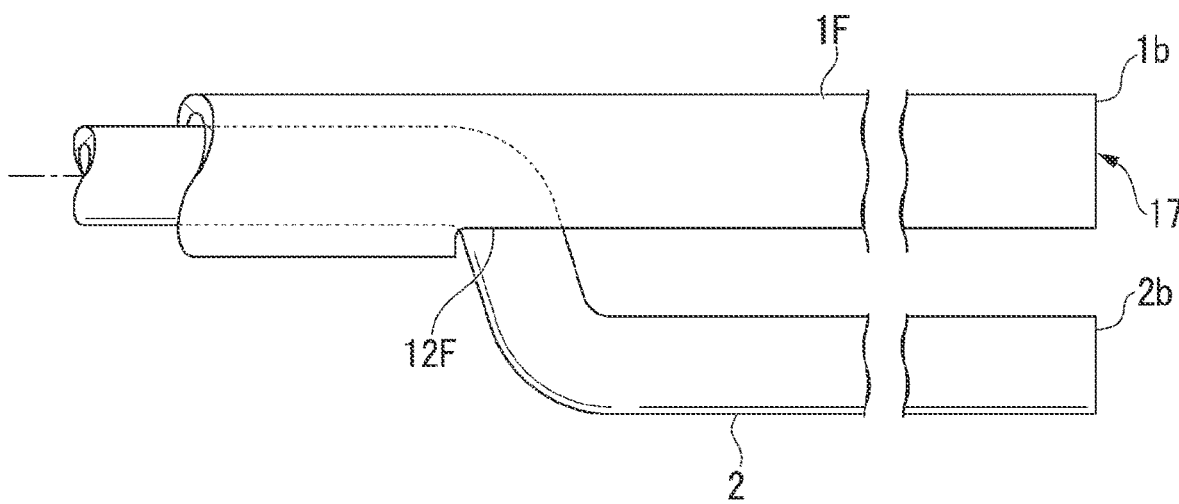
FIG. 12 is a view illustrating a modified example of a second opening in the outer tube.
Figure 13:
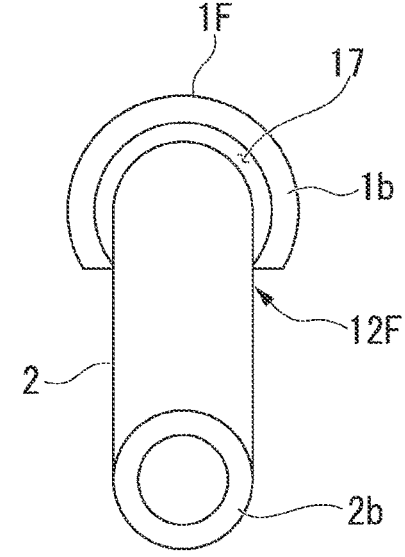
FIG. 13 is a view illustrating the outer tube viewed from the proximal end side.

For example, in the above embodiment, the second opening 12 or the like has substantially circular shape and formed in the intermediate portion of the outer tube 1 or the like, but the second opening is not limited to the type. FIG. 12 a view illustrating the outer tube 1F having the second opening 12F as the modified example of a second opening 12. FIG. 13 is a view illustrating the outer tube 1F viewed from the proximal end side. The second opening 12F is an opening extending to the proximal end 1b of the outer tube 1F. The second opening 12F communicates with the fourth opening 17 of the proximal end 1b of the outer tube 1F. Since the second opening 12F extends to the proximal end 1b of the outer tube 1F, the inner tube 2 is difficult to come into contact with the edge of the second opening 12F when the inner tube 2 moves, and the reaction force generated by the contact and making the inner tube 2 advance and retract is less likely to occur.

Although the second embodiment of the present invention has been described in detail with reference to the drawings hereinbefore, a specific configuration is not limited to the embodiment, and includes design changes without departing from the gist of the present invention. In addition, it is possible to combine and configure components shown in the embodiment described above and a modified example as appropriate.

What is claimed is:

1. A stent delivery system comprising:
an outer tube in which a first opening is formed in a distal end and a second opening is formed between the distal end and a proximal end;
an inner tube inserted into the outer tube from the first opening to the second opening, and disposed outside of the outer tube from the second opening to the proximal end of the outer tube; and
a stent stored in a storage position between the inner tube and the outer tube, wherein
the outer tube and the inner tube are configured to be inserted into a channel of an endoscope,
the second opening is formed at a position where the second opening is arranged inside the channel when the storage position is protruded from a distal end side of the channel.

2. The stent delivery system according to claim 1, wherein in a state that a storage location of the stent is protruded from a distal end of the channel, a length from the second opening to a forceps of the endoscope is longer than a longitudinal length of the stent.

3. The stent delivery system according to claim 1, wherein the outer tube include a first portion where is a distal end side portion from the second opening, and a second portion where is a proximal end side from the second opening,
an outer diameter of the first portion of the outer tube is larger than an outer diameter of the second portion of the outer tube.

4. The stent delivery system according to claim 3, wherein an opening surface of the second opening is perpendicular to a longitudinal direction of the outer tube.

5. The stent delivery system according to claim 3, wherein an opening surface of the second opening is inclined with respect to a longitudinal direction of the outer tube.

6. The stent delivery system according to claim 1, wherein
in the outer tube, a third opening is opened between the distal end and the proximal end of the outer tube,
in the inner tube, a distal end opening is opened at a distal end of the inner tube and an intermediate opening is opened between the distal end and a proximal end of the inner tube,
a guide wire inserted into the distal end opening passes through the intermediate opening and the third opening, and is extracted to an outside of the outer tube and the inner tube.

7. The stent delivery system according to claim 6, wherein the third opening is formed between the first opening and the second opening.

8. The stent delivery system according to claim 1, wherein rigidity of a distal end side is higher than rigidity of a proximal end side on at least one of the outer tube and the inner tube.

9. An endoscope system comprising:
a stent delivery system including an outer tube in which a first opening is formed in a distal end and a second opening is formed between the distal end and a proximal end;
an inner tube inserted into the outer tube from the first opening to the second opening, and disposed outside of the outer tube from the second opening to the proximal end of the outer tube, and including a stent stored between the inner tube and the outer tube; and
an endoscope having a channel into which the stent delivery system is insertable, wherein
the second opening is formed at a position where the second opening is arranged inside the channel when a storage position is protruded from a distal end side of the channel.

10. The endoscope system according to claim 9, wherein the endoscope has a fixing member fixing the inner member.

11. The endoscope system according to claim 9, wherein the outer tube include a first portion where is a distal end side portion from the second opening, and a second portion where is a proximal end side from the second opening,
an outer diameter of the first portion of the outer tube is larger than an outer diameter of the second portion of the outer tube.

12. The endoscope system according to claim 11, wherein an opening surface of the second opening is perpendicular to a longitudinal direction of the outer tube.

13. The endoscope system according to claim 11, wherein an opening surface of the second opening is inclined with respect to a longitudinal direction of the outer tube.

14. The endoscope system according to claim 9, wherein
in the outer tube, a third opening is opened between the distal end and the proximal end of the outer tube,
in the inner tube, a distal end opening is opened at a distal end of the inner tube and an intermediate opening is opened between the distal end and a proximal end of the inner tube,
a guide wire inserted into the distal end opening passes through the intermediate opening and the third opening, and is extracted to an outside of the outer tube and the inner tube.

15. The endoscope system according to claim 14, wherein the third opening is formed between the first opening and the second opening.

16. A stent indwelling method using an endoscope and a stent delivery device, the method comprising:

inserting the stent delivery system into a channel of the
endoscope;
inserting a distal end of the stent delivery system through
the channel to an indwelling position of a stent;
fixing an inner tube of the stent delivery system to the
endoscope after arriving the distal end of the stent
delivery system at the indwelling position;
exposing the stent housed between the inner tube and an
outer tube of the stent delivery system from the outer
tube by pulling the outer tube toward a proximal side,
the outer tube being provided in the stent delivery
system so as to cover the inner tube, wherein
in the outer tube, a first opening is formed in a distal end
and a second opening is formed between the distal end
and a proximal end,
the inner tube is inserted into the outer tube from the first
opening to the second opening and disposed outside of
the outer tube from the second opening to the proximal
end.
17. The stent indwelling method according to claim 16,
wherein when fixing the inner tube to the endoscope, the
inner tube is fixed to a portion of an operation portion of the
endoscope that surrounds a forceps plug.
18. The stent indwelling method according to claim 16,
wherein when inserting the stent delivery system into the
channel, the stent delivery system is inserted to a target
position through the channel by using a guide wire.
19. The stent indwelling method according to claim 16,
wherein when exposing the stent housed between the outer
tube and the inner tube from the outer tube, the second
opening is disposed inside the channel.

* * * * *

14